United States Patent
Chen et al.

(10) Patent No.: US 9,750,901 B2
(45) Date of Patent: Sep. 5, 2017

(54) DRY POWDER DRUG-DOSING DEVICE

(75) Inventors: Lan Chen, Shanghai (CN); Dizheng Du, Shanghai (CN); Lei Xu, Shanghai (CN)

(73) Assignee: SHANGHAI XIUXIN CHENPON PHARMACEUTICAL TECHNOLOGY CO., LTD., Zhangjiang High-Tech Park, Pudong New District, Shanghai (CN)

(*) Notice: Subject to any disclaimer, the term of this patent is extended or adjusted under 35 U.S.C. 154(b) by 868 days.

(21) Appl. No.: 14/125,936

(22) PCT Filed: Jun. 8, 2012

(86) PCT No.: PCT/CN2012/076647
§ 371 (c)(1),
(2), (4) Date: Dec. 12, 2013

(87) PCT Pub. No.: WO2012/171443
PCT Pub. Date: Dec. 20, 2012

(65) Prior Publication Data
US 2014/0137862 A1    May 22, 2014

(30) Foreign Application Priority Data
Jun. 13, 2011 (CN) .......................... 2011 1 0156768
Jun. 13, 2011 (CN) .......................... 2011 1 0156770

(51) Int. Cl.
*A61M 15/00* (2006.01)

(52) U.S. Cl.
CPC ....... *A61M 15/0065* (2013.01); *A61M 15/005* (2014.02); *A61M 15/0006* (2014.02); *A61M 2202/062* (2013.01); *A61M 2202/064* (2013.01)

(58) Field of Classification Search
CPC .......... A61M 15/0065; A61M 15/0006; A61M 15/005; A61M 15/0001; A61M 15/0025; A61M 2202/062; A61M 2202/064
See application file for complete search history.

(56) References Cited

U.S. PATENT DOCUMENTS

| | | | | |
|---|---|---|---|---|
| 5,429,122 A | * | 7/1995 | Zanen | A61M 15/0065 128/200.22 |
| 5,769,073 A | * | 6/1998 | Eason | A61M 15/0045 128/200.21 |
| 6,655,380 B1 | * | 12/2003 | Andersson | A61M 15/0065 128/203.15 |
| 2009/0050149 A1 | * | 2/2009 | Von Schuckmann | A61M 15/0065 128/203.15 |

* cited by examiner

*Primary Examiner* — Justine Yu
*Assistant Examiner* — Timothy Stanis
(74) *Attorney, Agent, or Firm* — Global IP Services; Tianhua Gu

(57) ABSTRACT

A dry powder drug-dosing device comprises a flow passage member (10), a drug powder storage container (19), and a drug-dosing metering component. A drug powder storage container (19), an annular manual rotation portion (3) and a rotational slide passage (23) are disposed on the outer surface of the housing. A sliding block (26) is disposed at an inner side of the annular manual rotation portion (3) A stirring gear (28) disposed on a transmission sleeve (27) is fit with the raised vibration tooth (21), so as to form a vibration component for enabling an outlet of the inverted conical drug powder storage container (19) to generate vibration. The dry powder drug-dosing device is applicable to the inhalation administration of various medicines in the form of dry powder.

14 Claims, 5 Drawing Sheets

DRY POWDER DRUG-DOSING DEVICE

CROSS REFERENCE TO RELATED PATENT APPLICATION

The present application is the US national stage of PCT/CN2012/076647 filed on Jun. 8, 2012, which claims the priorities of the Chinese patent applications No. 201110156770.1 filed on Jun. 13, 2011 and No. 201110156768.4 filed on Jun. 13, 2011, which applications are incorporated herein by reference.

FIELD OF THE INVENTION

The invention relates to instruments for the delivery of media into human body, especially, relates to a drug-dosing device for inhalation administration of a dry powder drug in a definite dose to the lung of the user.

BACKGROUND OF THE INVENTION

Drug delivery routes commonly comprise oral administration, inhalation, sublingual administration, external application, rectal administration, and injection, etc.

Since drugs can be absorbed into blood directly through the mucosa of mouth or nose after being inhaled orally or nasally, it can bypass the first-pass effect of the liver. The method of inhalation through mouth or nose is a most quick and effective way for the treatment of many diseases, of which asthma is the most common disease.

Nowadays, available devices of inhalation for the treatment of respiratory diseases such as asthma mainly include two types, the pressurized metered-dose inhalation device and the dry powder inhalation device.

For the aerosol-dosing device, with the improvement of environmental awareness both at home and abroad, chlorofluorocarbon (CFC) aerosols have been eliminated gradually. Chlorofluorocarbon, a haloalkane consisting of chlorine, fluorine and carbon, was used as a refrigerant in refrigerators at first, but its production was prohibited officially since 1 Jan. 1996 for its decomposition of the ozone layer. It is open for the study of new desirable aerosols.

On the other hand, if a pressurized metered-dose inhalation device is used, the user must coordinate the rhythm of spraying and inhalation well so as to obtain desirable drug inhalation effects.

The dry powder inhalation device is breath actuated, and there is no problem of rhythm coordination of spraying and inhalation.

Based on the type of drug storage, the dry powder inhalation device is divided into two types, isolated packages and one reservoir.

1). Dry Powder Inhalation Device with Isolated Packages:

Taking the commercially available Seretide accuhaler for instance, an inhalator described in a Chinese patent (Notice of Announcement No. CN 1313171C, Date of Announcement May 2, 2007) comprises a plurality of isolated cavities each of which contains a drug in a metered amount, and a lever which makes the cavities move one by one to align with the inhalation hole, wherein each cavity comprises an internal flange and an external rim, and said cavities are closed by sealing layers. The inhalator also comprises a mechanism for lifting the sealing layer away from the internal flange and external rim of the cavity so as to open the air passage formed by the cavity and the sealing layer. Therefore, when the user inhales from the pipe orifice, the drug powder in the cavity is carried by the air in the flow passage and taken out from the pipe orifice of the inhalator.

It is found in use that this type of dry powder inhalation device usually has a large volume and the manufacturing/purchasing cost is relatively high.

2) Dry Powder Inhalation Device with a Reservoir:

The representative of this type of dry powder inhalation device is commercially available product Turbuhaler.

A drug delivery device disclosed in a Chinese patent (Notice of Announcement No. CN 1054304C, Date of Announcement Jul. 12, 2000) comprises a powder vessel which can be filled with pulverized drug, and a measuring chamber connected with the powder vessel. The measuring chamber can separate the pulverized drug quantificationally from the vessel in batches.

An inhalation device disclosed in a Chinese patent (Notice of Announcement No. CN 1247275C, Date of Announcement Mar. 29, 2006) comprises a flow passage formed by a plurality of surfaces and a metering unit. The user's inspiration enables the airflow carrying with a dose of drug powder to pass through the flow passage; and the metering unit provides a dose of drug powder to the flow passage, so as to deliver the drug powder through the airflow.

It is clear that this type of dry powder inhalation device with a reservoir is usually equipped with a powder vessel and a corresponding metering component. The metering component separates the pulverized drug quantificationally from the powder cavern in batches.

A big problem of dry powder/micro powder administration is that the powder particles have high surface energy and are easy to form an agglomeration status, thus it is quite difficult to meter each dose of the storage drug.

Many attempts have been made to solve such a problem, for example, in Chinese patent ZL 91107979.3, a pressure is applied to the powder in the drug storage vessel via a spring. However, the force of the spring changes along with its length and the design flaw results in residual powder left in the device and/or leaking of powder; and also the mis-operation of over-dose can not be avoided.

However, since dry powder metering components in commercially available products and that disclosed in Chinese patent ZL 98805080.3, are through-holes, the leaking of powder occurs more frequently and the mis-operation of over-dose can not be avoided.

The drug measuring method in Chinese patent application 200780008580.7 also does not solve the problem of metering accurately when the dry powder is in a small quantity.

The international patent application with publication number of WO2008/001744 discloses a drug-dosing device with a vibration unit on the housing, which can produce vibration when the upper cover of the device is open. The purpose of setting this vibration unit is to make the drug powder to enter the measuring structure perfectly. However, it is difficult to judge how much contribution it makes to the drug powder to enter the measuring structure by vibrating the whole drug-dosing device.

Moreover, in commercially available dry powder inhalation devices with a reservoir, the air inlet/hole connected with the flow passage is usually equipped on the housing. When the protective cover of the dry powder device is removed, the air inlet is exposed in the air and the air channel connected with the powder vessel (air inlet/hole-flow passage-powder vessel-mouthpiece) is always in open status. The moisture in the air entered into the powder vessel

SUMMARY OF THE INVENTION makes the drug powder to be damp and caking easily and influences the accuracy of dosing and the use efficiency of the device.

To solve the moisture adsorption problem of dry power drug, a completely sealing structure of mouthpiece and air inlet is adopted in the device and the drug powder metering structure/component is dried before the drug powder is filled in each time, thus preventing the drug dry powder from being damped and caked; meanwhile a drug-dosing metering structure with drug-dosing cavities is adopted, thus avoiding disadvantages of over-dose and drug powder leakage; moreover, the outlet of the powder storage container of the dry powder drug-dosing device is equipped with a structure for vibrating the drug-dosing unit in order to assist the fine powder flow, thus metering the drug powder accurately.

Specifically, the invention provides a dry powder drug-dosing device, at least comprising a flow passage member, a drug powder storage container and a drug-dosing metering component, and said flow passage member containing a mouthpiece and a flow passage element, characterized in: a housing constituted by an upper body and a lower body; an inverted conical drug powder storage container disposed in the upper part of the housing; an annular manual rotation portion disposed outside the upper part of the housing; a rotational slide passage disposed on the outer surface of the upper part of the housing and a sliding block disposed at the inner side of the annular manual rotation portion correspondingly; a first elastic member disposed in the cavity between the annular manual rotation portion and the upper part of the housing; a gas inlet disposed at an end of the rotation slide passage; a flow passage member disposed in the housing; a mouthpiece disposed in the outside of the housing and a cap disposed in the outside of the mouthpiece; the head end of said flow passage element connecting to the gas inlet, the tail end of the flow passage element connecting to the mouthpiece air channel and the horizontal portion of the flow passage member having an opening as drug inlet; a drug-dosing metering component disposed below the inverted conical drug powder storage container; and said flow passage element connected to the gas inlet, the drug-dosing metering component and the mouthpiece in sequence via an air channel.

In a preferable embodiment, the rotation slide passage circuit comprises an upper slide passage and a lower slide passage which are parallel to each other, and the first and second lifting slide passages connected to the head and tail ends of the upper and lower slide passages; the annular manual rotation portion can rotate in a restricted angle and ascend/descend at designated positions on the upper body under the guidance/limitation/effects of the upper/lower slide passages, the first/second lifting slide passages, the sliding block and the first elastic member.

In a preferable embodiment, the restricted angle is 120°; and the designated positions are the positions of head and tail ends of the upper and lower slide passages.

In a preferable embodiment, at least one gas inlet is installed to pass through the housing of the lower slide passage.

In a preferable embodiment, the drug-dosing metering component comprises a ration drug-dosing plate with a central axis, a spring cover under the ration drug-dosing plate and a second elastic member positioned between the lower body and the spring cover; the head end of said central axis passes through the upper part of the upper body and a triangle block is provided at the head end of the central axis; a triangle hole is provided correspondingly in the center of said annular manual rotation portion; the tail end of said central axis is connected to the lower body rotatably; three drug-dosing cavities are distributed uniformly along the circumference on the side of the ration drug-dosing plate towards the inverted conical drug powder storage container; and the drug inlet of the flow passage member is arranged correspondingly to one of the three drug-dosing cavities.

In a preferable embodiment, three elastic locating clips are distributed uniformly on the circumference of the ration drug-dosing plate; and three positioning grooves are distributed correspondingly in the internal side of the lower body; the elastic locating clips match with the positioning grooves to ensure the rotational range of the ration drug-dosing plate is ⅓ of the circumference every step and a definite signal of "rotation in place" is given to the user.

In a preferable embodiment, the first elastic member or the second elastic member is a spring.

In a preferable embodiment, the upper part of the upper body is provided with a drying component consisting of a drying cylinder and granular desiccant therein; the drying cylinder has an opening in the direction identical to the outlet of the inverted conical drug powder storage container; the drying component and the inverted conical drug powder storage container are arranged in an included angle of 120° relative to the longitudinal central axis of the housing; the opening of the drying component or the outlet of the inverted conical drug powder storage container is arranged to be corresponding to two of the three drug-dosing cavities distributed along the circumference of the ration drug-dosing plate of the drug-dosing metering component.

In a preferable embodiment, a locking block is set on the annular manual rotation portion, when the mouthpiece cap is in covered status, the locking block cooperates with the mouthpiece cap to form an anti-maloperation mechanical structure, so as to prevent the happening of rotation between the annular manual rotation portion and the upper body.

The invention also provides a process for inhalation administration using the dry powder drug-dosing device, comprising steps of filling drug powder, getting ready for inhalation and drying empty cavity. Each cavity is dried first, then filled with the drug.

Specifically, the invention provides a dry powder drug-dosing device, characterized in completing the whole inhalation administration in steps of:

A. removing the mouthpiece cap;

B. manually rotating the annular manual rotation portion counterclockwise to an extreme position of 120°;

C. the annular manual rotation portion springing upward automatically;

D. manually rotating the annular manual rotation portion reversely to a reverse extreme position of 120°;

E. inhaling the drug powder via the mouthpiece;

F. pressing down the annular manual rotation portion manually; and

G. covering the mouthpiece cap.

Furthermore, the dry powder drug-dosing device completes the whole procedures of cavity drying-drug supplying-drug-providing in the sequence of:

A1. removing the mouthpiece cap and releasing the anti-misrotation mechanical limit on the annular manual rotation portion;

B1. manually rotating the annular manual rotation portion counterclockwise to an extreme position of 120° to enable the first drug-dosing cavity of the ration drug-dosing plate in said drug-dosing metering component to receive the drug supplied from the inverted conical drug powder storage container;

C1. the annular manual rotation portion springing upward automatically and the air inlet opening to provide a condition for inhalation administration; meanwhile, the triangle block at the head end of the central axis of said drug-dosing metering component entering the triangle hole in the center of the annular manual rotation portion to provide a precondition for the next rotation of the ration drug-dosing plate;

D1. manually rotating the annular manual rotation portion reversely to a reverse extreme position of 120°; and the first drug-dosing cavity with drug powder aiming at the drug inlet of the flow passage member to finish the drug supplying process;

E1. inhaling the drug powder through the mouthpiece, wherein the gas enters the dry powder drug-dosing device from the air inlet and passes the flow passage member to reach the drug inlet, then delivers the drug powder from the first drug-dosing cavity of the ration drug-dosing plate to the patient's mouth via the mouthpiece, and the drug delivering process is finished;

F1. manually pressing down the annular manual rotation portion to enable the second drug-dosing cavity of the ration drug-dosing plate in said drug-dosing metering component to aim at the drying component for drying and preparing for the next drug-filling; and G1. covering the mouthpiece cap and restoring the anti-misrotation mechanical limit on the annular manual rotation portion.

The invention also provides a vibrating drug-providing unit equipped on the dry powder drug-dosing device, said dry powder drug-dosing device comprising a housing consisting of an upper body and a lower body, a drug powder storage container and a drug-dosing metering component in the housing, a mouthpiece on the outside of the housing, a flow passage member at the inside of the housing, and the flow passage member connecting to the air inlet, the drug-dosing metering component and the mouthpiece in sequence, characterized in that an inverted conical drug powder storage container is disposed in the upper part of the housing; an annular manual rotation portion is disposed outside the upper part of the housing; a drug-dosing metering component comprising a center rotating axis and a ration drug-dosing plate is disposed under said inverted conical drug powder storage container; the center rotating axis of the drug-dosing metering component is connected to the annular manual rotation portion by the meshing of triangle components, the block on the center rotating axis and the hole on the annular manual rotation portion; a protruding vibration tooth is disposed at the lower part of the inverted conical drug powder storage container; a transmission sleeve is disposed inside the lower end of the annular manual rotation portion; the upper end of the transmission sleeve is fixedly connected to the annular manual rotation portion; the transmission sleeve coaxially set outside the central rotating axis; a stirring gear is disposed at the lower end of the transmission sleeve; and the protruding vibration tooth cooperates with the stirring gear to form a vibration component to enable the outlet of the inverted conical drug powder storage container to vibrate.

Specifically, the transmission sleeve and the stirring gear at the lower end thereof rotate/ascend/descend synchronously with the annular manual rotation portion when the annular manual rotation portion rotates/ascends/descends.

The vibration component enables the outlet of the inverted conical drug powder storage container to vibrate when the transmission sleeve is put in motion by the rotation of the annular manual rotation portion.

When the annular manual rotation portion is in the original or descending position, the stirring gear contacts/meshes with the protruding vibration tooth; the stirring gear rotates along with the annular manual rotation portion, and the stirring teeth on the stirring gear drive the protruding vibration tooth to vibrate and then to drive the outlet of the inverted conical drug powder storage container to vibrate, thus to fulfill vibrating drug-providing.

When the annular manual rotation portion is in an ascending or springing position, the transmission sleeve and the stirring gear at the lower end thereof ascend synchronously; and the stirring gear is out of contact with the protruding vibration tooth.

At least ⅓ of circumference of the stirring gear is equipped with stirring teeth; and the section of the circumference with stirring teeth is correspondingly in the horizontal position, so as to keep the stirring teeth in contact with the protruding vibration tooth in the range of the rotation angle of the stirring gear.

In comparison with the prior art, the invention has the following advantages:

1. A double full-sealed structure is used in the device. Only during a short period of the mouthpiece cap being in "removed" status and the annular manual rotation portion springing after the first rotation, the inlet and outlet of the flow passage of the dry powder drug-dosing device will connect to the outside air. After the user inhales the drug powder and presses down the annular manual rotation part manually, the connection of the flow passage with the air outside is cut of again, thus avoiding the problem that "the flow passage is always in 'open' status when the protective cover is removed" and further reducing the possibility of the drug dry powder in the powder container to be damped and caked.

2. A structure with three drug-dosing cavities, not through-holes, is provided, so the problem of "powder leakage" or "over dose" can be avoided.

3. Since a drying component is equipped, the drug powder metering component/structure, each drug-dosing cavity of the drug-dosing plate, is dried before the drug powder is filled each time. Along with the rotation of the ration drug-dosing plate, each drug-dosing cavity moved under the outlet of the inverted conical drug power storage container has always been dried. The accuracy of dose is ensured by using this operational mode of "drying first and then filling with the drug" for each drug-dosing cavity;

4. The structure of the inverted conical drug powder storage container and the vibration unit arranged at the outlet thereof further ensure the accuracy of dose;

5. The vibration mode of the stirring gear-vibration tooth is independent of the elastic member, and it is not influenced by the change of storage volume of the drug powder;

6. The operation sequence of "filling drug→ready for inhalation→drying" is adopts in the dry powder drug-dosing device, and the operational mode of "drying first and then drug filling" is adopted for each drug-dosing cavity. Therefore, the drug power dose can be metered accurately.

7. An anti-misrotation mechanical structure is equipped on the annular manual rotation portion. It prevents abnormal rotation between the annular manual rotation portion and the upper body, and ensures the sealing effect of the flow passage, thus avoiding accidental drug-delivery and eliminating abnormal loss of the stored drug powder.

In the figures, 1 is the central rotating axis, 1-1 is the central rotating axle hole, 2 is the locking block, 3 is the annular manual rotation portion, 8 is the upper body, 10 is the flow passage member, 10-1 is the head end of the flow passage, 10-2 is the tail end of the flow passage, 10-3 is the drug inlet of the flow passage, 11 is the mouthpiece, 12 is the air inlet, 13 is the drug-dosing plate, 14 are drug-dosing cavities, 15 is the spring cover, 16 is the lower body, 17 is the drying cylinder, 19 is the inverted conical drug powder storage container, 20 is the second elastic member, 21 is the vibration tooth, 23 is the rotation slide passage, 23-1 is the upper slide passage, 23-2 is the lower slide passage, 23-3 is the first lifting slide passage, 23-4 is the second lifting slide passage, 24 is elastic locating clip, 25 is the first elastic member, 26 is the sliding block, 27 is the transmission sleeve, 28 is the stirring gear, 29 is positioning groove on the lower body, 30 is the triangle block, 31 is the triangle hole.

DESCRIPTION OF PREFERRED EMBODIMENTS

Figure 1:
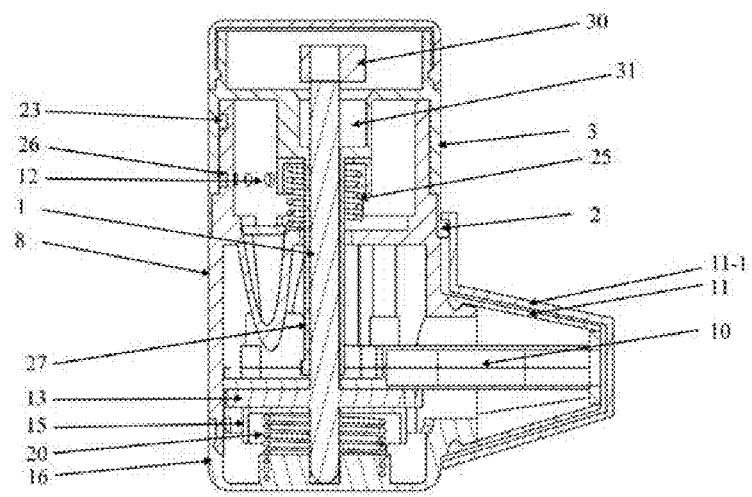
FIG. 1 is a sectional structure diagram of the dry powder drug-dosing device.
Figure 2:
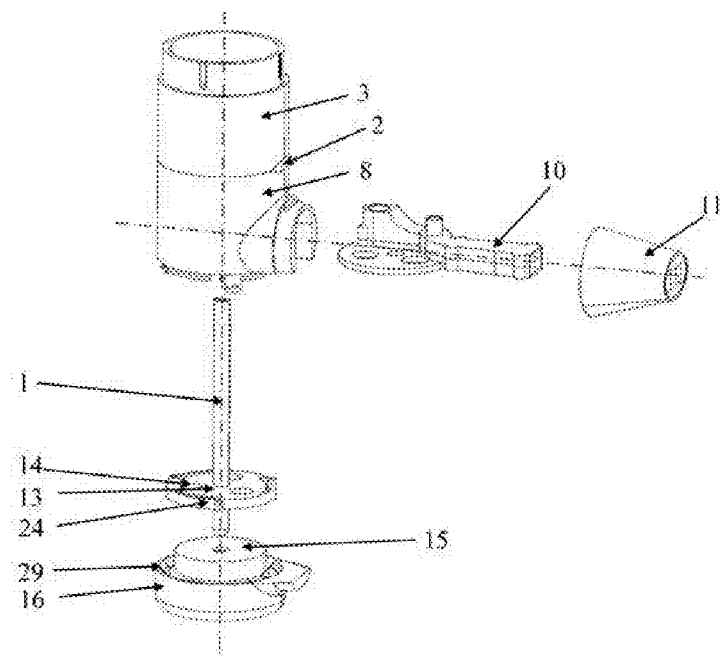
FIG. 2 is a three-dimensional breakdown structure diagram of the dry powder drug-dosing device.

In FIG. 1 and FIG. 2, the dry powder drug-dosing device comprises a housing consisting of an upper body 8 and a lower body 16.

An inverted conical drug powder storage container (refer to the component 19 shown in FIG. 3) is equipped on the upper part of the housing; an annular manual rotation portion 3 is provided at the periphery of the upper part of the housing; a rotation slide passage 23 is equipped on the external surface of the upper part of the housing, and a sliding block 26 is equipped correspondingly at the internal side of the annular manual rotation portion; a first elastic member 25 is provided in the cavity between the annular manual rotation portion and the upper part of the housing; the air inlet(s) 12 is/are equipped on the rotation slide passage of the housing; a flow passage member 10 is provided inside the housing; a mouthpiece 11 is disposed at the external side of the housing; a mouthpiece cap is provided outside the mouthpiece.

A drug-dosing metering component is equipped under the inverted conical drug powder storage container, comprising a ration drug-dosing plate 13 with a central rotating axis 1, a spring cover 15 located under the ration drug-dosing plate and a second spring 20 between the lower body and the spring cover.

A vibrating drug-dosing component (refer to FIG. 8 or FIG. 9) consisting of a protruding vibration tooth 21 under the inverted conical drug powder storage container and a stirring gear 28 arranged at the lower end of the transmission sleeve 27 is provided at the outlet of the inverted conical drug powder storage container.

The flow passage member is connected to the air inlet, the drug-dosing metering component and the mouthpiece in sequence.

Drug-dosing cavities 14 are distributed uniformly along the circumference on the ration drug-dosing plate.

The drug-dosing cavities are in dose proximity to the bottom of the outlet of the inverted conical drug powder storage container. Drug powder flows from the inverted conical drug powder storage container into one of the drug-dosing cavities of the ration drug-dosing plate. The full cavity of drug powder is one dose for a user to inhale.

Since drug-dosing cavities are not through-holes, the central rotating axis drives the ration drug-dosing plate to rotate and administrate the drug in an accurate dose.

Three elastic locating clips 24 are arranged uniformly along the circumference of the ration drug-dosing plate and three positioning grooves 29 are arranged correspondingly at the internal side of the lower body. The elastic locating clips match with the positioning grooves to give the user a definite signal of rotation in place during the rotation process of the drug-dosing plate and to ensure that the rotation range of the ration drug-dosing plate is ⅓ of the circumference.

In a preferable embodiment, the first elastic member or the second elastic member is a spring.

Figure 3:
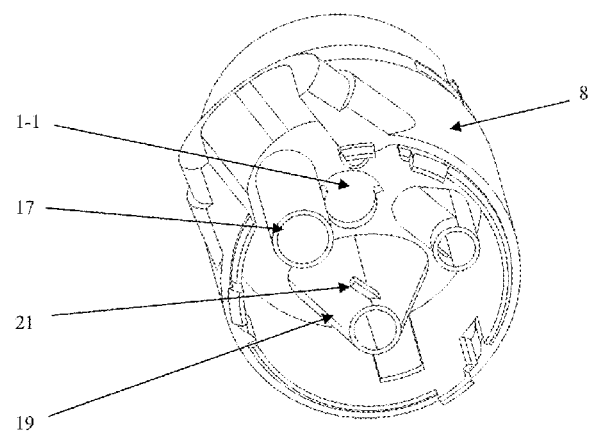
FIG. 3 is a structure diagram of the drying component and the inverted conical drug powder storage container.

In FIG. 3, an inverted conical drug powder storage container 19 with a downward outlet is equipped on the upper part of the housing (the upper body 8 in the Figure).

Meanwhile, the upper part of the housing is equipped with a drying component consisting of a drying cylinder 17 and granular desiccant therein. The drying cylinder has an opening in the direction identical to the outlet of the inverted conical drug powder storage container.

The drying component and the inverted conical drug powder storage container are arranged in an included angle of 120° relative to the longitudinal central axis of the housing (In the figure, the central line of axle hole 1-1 of the central rotating axis represents the longitudinal central axis).

The drug-dosing cavities are arranged on a horizontal circumference with an identical radius corresponding to the outlets of the drying component and the inverted conical drug powder storage container. In other words, the outlets of the drying component and the inverted conical drug powder storage container are arranged corresponding to the horizontally distributed circumference of the three drug-dosing cavities 14 of the ration drug-dosing plate 13 in FIG. 2.

When one drug-dosing cavity rotated along with the ration drug-dosing plate is underneath the outlet of the inverted conical drug powder storage container, the dry powder drug therein is filled into this drug-dosing cavity. Since the drug-dosing cavities fit tightly to the bottom of the outlet of the inverted conical drug powder storage container and they are not through-holes as well, an accurate dose can be administrated when the central axis drives the ration drug-dosing plate to rotate and "drug powder leakage" and "over dose" can be avoided.

In the same way, when one drug-dosing cavity rotated along with the ration drug-dosing plate is underneath the opening of the drying cylinder of the drying component, this drug-dosing cavity will be dried.

In accordance with the rotation direction of the ration drug-dosing plate, anyone of the drug-dosing cavities passes below the outlet of the drying cylinder first (drying), then passes below the outlet of the inverted conical drug powder storage container (drug filling), and at last passes below the drug inlet under the flowing component (drug inhalation). During a whole process of the inhalation of the drug powder, the three drug-dosing cavities are rotating circularly (actually, the ration drug-dosing plate with drug-dosing cavities is rotating directionally and circularly), so as to fulfill the whole operation process of "drying, drug powder filling, and drug powder inhalation".

Figure 4:
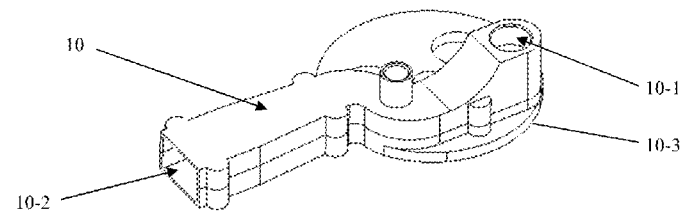
FIG. 4 is a structure diagram of the flow passage member.
Figure 5:
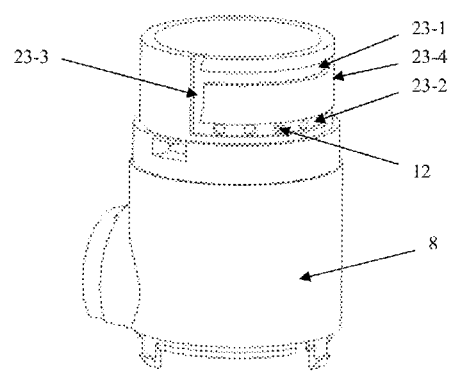
FIG. 5 is a structure diagram of the rotating/lifting slide passage on the upper body and position of the air inlet.
Figure 6:
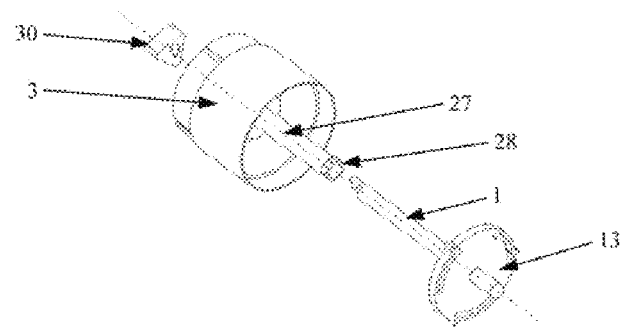
FIG. 6 is a structure diagram of the triangle block, the annular manual rotation portion, the central rotating axis and the transmission sleeve components.

In FIG. 4, the flow passage member 10 is an air passage component with openings at both head and tail ends, and a drug inlet under the middle horizontal section. This flow passage member provides a compulsive flowing direction/flow passage for the drug-carrying air.

The head end 10-1 of the flow passage member is connected to the air inlet (marked as 12 in the figure) on the upper body of the housing in FIG. 1 through the air circuit; the tail end 10-2 of the flow passage member is connected to the mouthpiece 11 in FIG. 1 through the air circuit; a drug inlet 10-3 with downward opening is set under the middle section/horizontal part of the flow passage member (because it opens downward, it is only shown by a mark in the figure).

The drug inlet of the flow passage member is located corresponding to the three drug-dosing cavities distributing along the circumference of the ration drug-dosing plate, and is in close proximity and directing to the drug-dosing cavities in the ration drug-dosing plate.

It is known, from FIG. 2, that the flow passage member is connected to the air inlet, the drug-dosing metering component (actually, the drug-dosing cavities in the ration drug-dosing plate) and the mouthpiece in sequence through the air circuit.

The flow passage in an arc design has no flow blind angle, thus no residual drug powder exists and the accuracy of dose is ensured.

In FIG. 5, the rotational slide passage (marked as 23 in FIG. 1) on the external surface of the upper part of the housing, i.e., the external surface of the upper body 8, is consisting of parallel upper rotational slide passage 23-1 and lower rotational slide passage 23-2, and first lifting slide passage 23-3 and second lifting slide passage 23-4 which connect the head and tail ends of the upper and lower rotational slide passages.

A sliding block 26 is equipped correspondingly at the internal side of the annular manual rotation portion (refer to the marked component 26 in FIG. 1).

The annular manual rotation portion 3 shown in FIG. 1 can rotate in a restricted angle on the upper body 8 and can ascend/descend in a designated position under the guidance/limitation effects of the upper/lower rotational slide passages, the first/second lifting slide passages, the sliding block and the first elastic member shown in FIG. 5.

The restricted angle is 120°.

The designated position is the head/tail end of the upper and lower rotational slide passages.

Furthermore, the air inlets 12 are equipped on the rotational slide passage of the housing.

Only in the short period of the mouthpiece cap 11-1 being in "removed" status and the annular manual rotation portion springing after the first rotation, the carrier air channel of the dry powder drug-dosing device, air inlet→flow passage→mouthpiece, can be connected to the air outside.

After the user inhales the drug powder and presses down the annular manual rotation portion manually, the carrier air channel connected to the air outside is cut off again, thus avoiding the problem that "the carrier air channel is always in 'open' status when the protective cover is removed" and further reducing the possibility of the drug dry powder in the powder vessel to be damped and caked.

In FIG. 6, the vibrating drug-dosing component is consisting of a protruding vibration tooth (refer to FIG. 3) equipped on the lower part of the inverted conical drug powder storage container and a stirring gear 28 equipped at the lower end of the transmission sleeve 27. The upper end of the transmission sleeve is fixedly connected to the annular manual rotation portion 3, and the transmission sleeve is sleeved on the central rotating axis coaxially (refer to FIG. 1).

When the annular manual rotation portion rotates or ascends or descends, the transmission sleeve and the stirring gear at its lower end rotate or ascend or descend synchronously with the annular manual rotation portion. When the transmission sleeve is driven by the annular manual rotation portion to rotate, the vibration component enables the outlet of the inverted conical drug powder storage container to vibrate.

In other words, during the rotation process of the transmission sleeve, the stirring gear and the protruding vibration tooth in the vibration component collide constantly, thus knocking the drug outlet of the inverted conical drug powder storage container to enable the drug powder to flow smoothly and the dose to be metered accurately.

In FIG. 7, the central axis 1 passes through the upper part of the upper body 8 and the annular manual rotation portion 3; and a triangle block 30 is mounted on the head end of the central axis.

A triangle hole 31 is provided correspondingly in the center of the top part of the annular manual rotation portion.

When the annular manual rotation portion 3 rotates/ascends under the guidance of the rotational slide passage and the first spring, the triangle block at the head end of the central axis is just inserted into the triangle hole. Due to the transmission action of the triangle hole-triangle block, the rotation of the annular manual rotation portion drives the central axis to rotate so as to drive the ration drug-dosing plate to rotate.

When the annular manual rotation portion descends under a downward external force, the triangle block is taken off from the triangle hole and the rotation of the annular manual rotation portion will not be transmitted to the ration drug-dosing plate. In this way, the drug-dosing metering component (central axis-ration drug-dosing plate) can be rotated directionally and the process of "drying→drug supplying→drug-dosing" can be achieved.

It can also be seen from this figure that the three drug-dosing cavities 14 are uniformly arranged on the ration drug-dosing plate 13 which is fixedly connected to the central axis.

In FIG. 8 and FIG. 9, stirring teeth are equipped on at least ⅓ of circumference of the stirring gear 28 and the section of circumference having stirring teeth in the stirring gear is arranged correspondingly to the horizontal position of the protruding vibration tooth 21, so as to ensure the constant contact between the stirring teeth and the protruding vibration tooth within the range of the rotation angle of the stirring gear.

The protruding vibration tooth is fixed on the lower part of the inverted conical drug powder storage container and the stirring gear 28 is equipped at the lower end of the transmission sleeve 27, while the upper end of the transmission sleeve is fixedly connected to the annular manual rotation portion 3. Therefore, only when the annular manual rotation portion is in the original position or the descending position, the stirring gear contacts to the protruding vibration tooth and rotates along with the rotation of the annular manual rotation portion; then the stirring tooth on the stirring gear drives the protruding vibration tooth to vibrate so as to further drive the outlet of the inverted conical drug powder storage container to vibrate and fulfill the vibrating drug providing.

When the annular manual rotation portion is in an ascending position or bounced position, the transmission sleeve and the stirring teeth at its lower end ascend synchronously with the annular manual rotation portion, thus separating the stirring gear away from the protruding vibration tooth.

Figure 8:
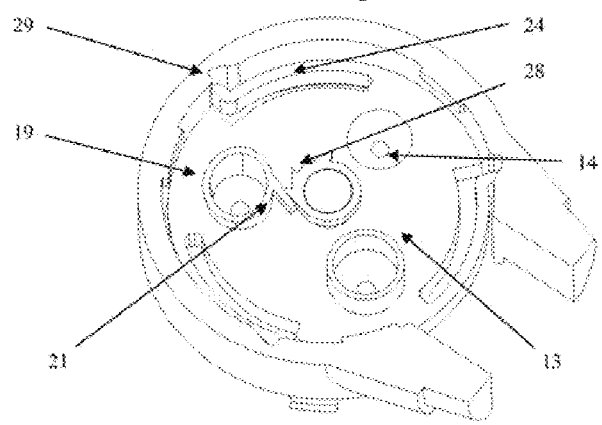
FIG. 8 is a structure diagram of the vibrating drug-dosing unit.

It can also be seen from FIG. 8 that three elastic locating clips 24 are arranged uniformly on the circumference of the ration drug-dosing plate 13, and three positioning grooves 29 are arranged correspondingly at the internal side of the lower body. The match of the elastic locating clips with the positioning grooves gives the user a definite signal of rotation in place and ensures the rotating range of the ration drug-dosing plate being ⅓ of the circumference every time when the ration drug-dosing plate is rotating.

It is also known from FIG. 8 that the drying component (shown as a drying cylinder 17 in the figure) and the outlet 19 of the inverted conical drug powder storage container are arranged in an included angle of 120° relative to the longitudinal central axis of the housing.

Figure 9:
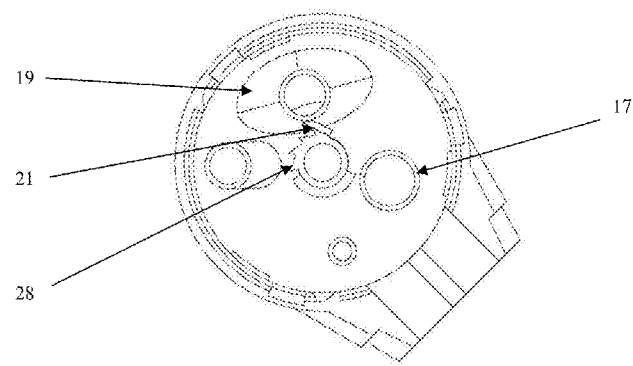
FIG. 9 is a structure diagram of the vibration component.

In fact, FIG. 8 is a top view showing the position relation between the ration drug-dosing plate and the vibrating drug-dosing component thereon; and FIG. 9 is an upward view of the ration drug-dosing plate showing the position relation between the lower end part on the upper body and the vibrating drug-dosing component thereon.

The dry powder drug-dosing device of the invention fulfills the whole processes of inhalation administration in the following steps.

Step 1. Removing the mouthpiece cap and releasing the anti-misrotation mechanical limit on the annular manual rotation portion.

Locking block 2 disposed on the annular manual rotation portion can prevent mis-operation when the user rotates the annular manual rotation portion before removing the mouthpiece.

Figure 10:
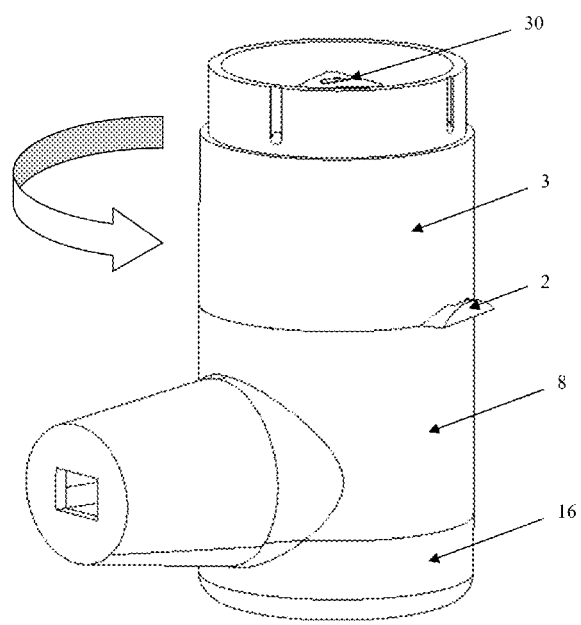
FIG. 10 is an operation diagram when the annular manual rotation portion is rotated counterclockwise.

Step 2. The user manually rotates the annular manual rotation portion counterclockwise to an extreme position of 120° as shown in FIG. 10.

When the annular manual rotation portion is rotated, the transmission sleeve fixedly connected therebelow and the stirring gear at its lower end rotate synchronously with the annular manual rotation portion.

When the transmission sleeve is driven by the annular manual rotation portion to rotate, the stirring gear contacts/meshes with the protruding vibration tooth. The stirring gear rotates along with the rotation of the annular manual rotation portion, and the stirring teeth on the stirring gear drive the protruding vibration tooth to vibrate so as to drive the outlet at the lower part of the inverted conical drug powder storage container to vibrate, thus realizing the function of "vibrating drug providing".

At this time the first drug-dosing cavity of the ration drug-dosing plate in the drug-dosing metering component was filled with the drug powder from the inverted conical drug powder storage container to fulfill the drug-dosing.

When the annular manual rotation portion is rotated in an angle of 120°, the protruding sliding block 26 in the inner wall thereof slides from the lower left corner to the lower right corner counterclockwise along the lower rotational slide passage on the upper body. The Whole process is 120°.

Figure 11:
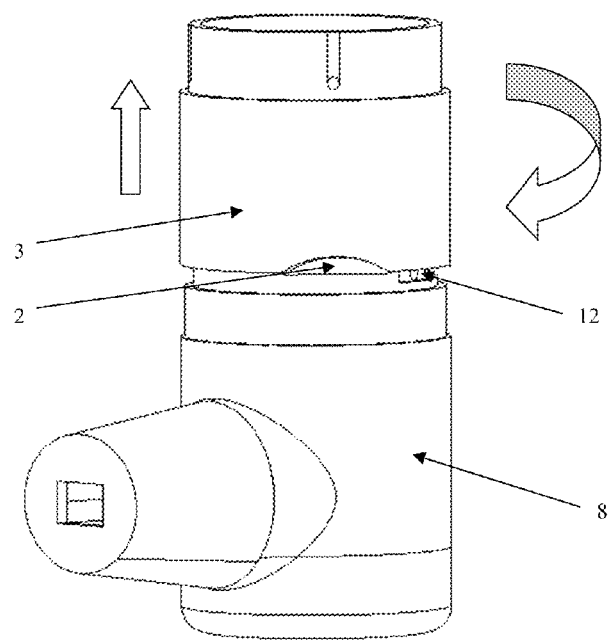
FIG. 11 is an operation diagram when the annular manual rotation portion is rotated clockwise.

Step 3. As shown in FIG. 11, the annular manual rotation portion 3 bounces upward automatically, and the air inlet(s) 12 open to get ready for the inhalation administration.

When the sliding block reaches the lower right position of the lower rotational slide passage, the whole annular manual rotation portion 3 is upspringing due to the effect of the first spring, and the air inlet(s) 12 which is/are on the lower rotational slide passage and runs through the housing 8 is/are exposed in air at this moment. Therefore, the air inlet(s) is/are connected to the outside air and the user can inhale the drug powder.

Figure 7:
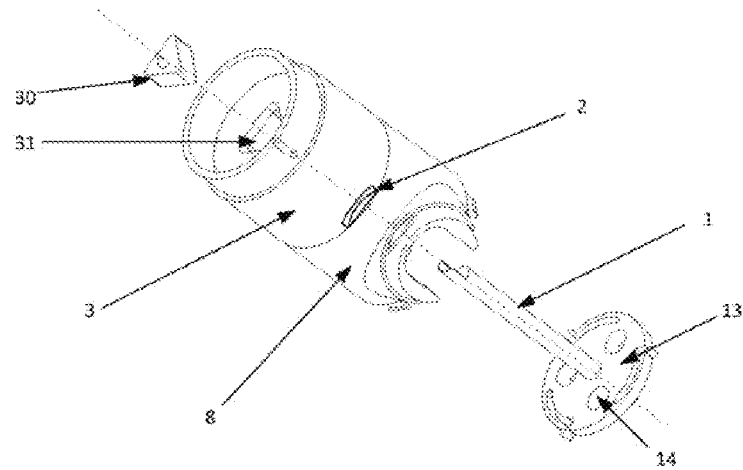
FIG. 7 is a transmission structure diagram among the triangle block, the annular manual rotation portion and the central axis.

When the annular manual rotation portion 3 is upspringing, the triangle hole (component 31 in FIG. 7) on the annular manual rotation portion ascends and just meshes with the triangle block (component 30 in FIG. 7 and FIG. 10). At this time, the transmission sleeve on the annular manual rotation portion and the stirring gear at the lower end of the transmission sleeve ascend synchronously, thus the stirring gear is out of touch with the protruding vibration tooth.

Step 4. Rotating the annular manual rotation portion clockwise to the extreme position of 120° again As shown in FIG. 11 the user rotates again the annular manual rotation portion 3 to 120° clockwise, and the sliding block at the internal side of the annular manual rotation portion slides to the upper left corner on the upper rotational slide passage. Since the triangle block meshes with the triangle hole, the rotation of 120° of the annular manual rotation portion drives the ration drug-dosing plate to rotate 120° correspondingly so as to enable the drug-dosing cavity filled with drug powder to move to the drug inlet on the bottom of the flow passage to get ready for the user to inhale the drug powder.

Step 5. The user inhales the drug powder through the mouthpiece

The air for carrying the drug powder enters the dry powder drug-dosing device from the air inlet, and flows along the flow passage member to the drug inlet so as to deliver the drug powder in the first drug-dosing cavity of the ration drug-dosing plate to the mouth of the user through the mouthpiece, and the drug-dosing process is finished.

Step 6. The drug-dosing cavity is dried for preparing the next drug providing.

Figure 12:
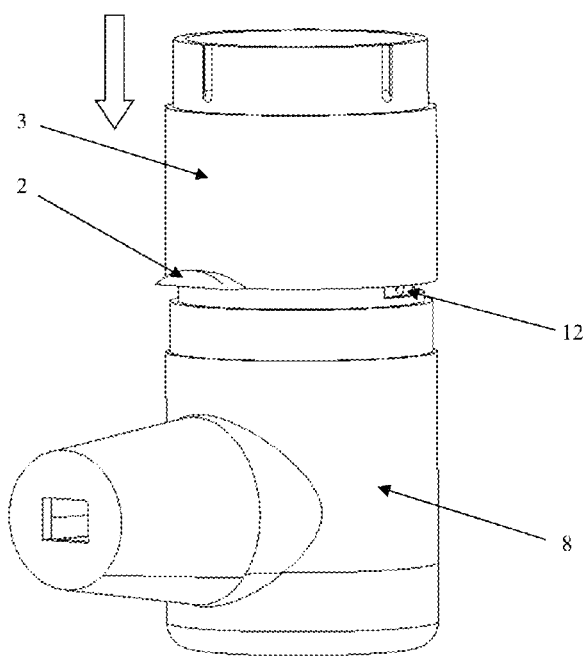
FIG. 12 is an operation diagram when the annular manual rotation portion is pressed down and the drug-dosing is finished.

As shown in FIG. 12, the user only needs to press down the annular manual rotation portion 3 to separate the triangle block away from the triangle hole, thus the annular manual rotation portion is in the initial position for use next time.

At last, put the mouthpiece cap on to seal the air inlet and restore the anti-misrotation mechanical restriction to the annular manual rotation portion. The whole drug-providing process is finished.

In the later use, the above steps are repeated, and the three drug-dosing cavities of the ration drug-dosing plate are always rotated clockwise and in the procedure of "vibrating drug-providing→ready for inhaling→drying".

Above-mentioned examples are only used to explain and describe the invention but not to limit the technical solution of the invention. Those skilled in the art should know that any change or modification of the examples is within the scope of attached Claims without departing from the spirit of the invention.

INDUSTRIAL APPLICABILITY

The technical solution adopts a double full-sealed mouthpiece and air inlet method, and each drug-dosing cavity is operated in the mode of "being dried first and then filled with drug", thus preventing the drug powder from damping and caking and fulfilling accurate metering of the drug powder.

Meanwhile, the rotation/lift of the annular manual rotation portion drives the ration drug-dosing plate to rotate to make each drug-dosing cavity to be "dried first and then filled with drug".

Moreover, a vibration component equipped at the lower part of the inverted conical drug powder storage container makes the vibration of the outlet of the inverted conical drug powder storage container, thus forming "vibrating drug-providing".

Moreover, elastic locating clips and positioning grooves respectively equipped on the ration drug-dosing plate and the lower body ensure the angle of each rotation of the ration drug-dosing plate, and gives the user a definite signal of "rotation in place", thus bringing convenience to the user and making the operation accurate and simple.

The technical solution is applicable to the design and manufacture of dry powder drug-inhalation device.

What is claimed is:

1. A dry powder drug-dosing device, at least comprising a flow passage member, a drug powder storage container and a drug-dosing metering component, and said flow passage member containing a mouthpiece and a flow passage element, the dry powder drug-dosing device characterized by:
   a housing constituted by an upper body and a lower body;
   an inverted conical drug powder storage container disposed in an upper part of the housing;
   an annular manual rotation portion disposed outside the upper part of the housing;
   a rotational slide passage disposed on an outer surface of the upper part of the housing and a sliding block disposed at an inner side of the annular manual rotation portion correspondingly;
   a first elastic member disposed in a cavity between the annular manual rotation portion and the upper part of the housing;
   a gas inlet disposed at an end of the rotational slide passage;
   the flow passage member disposed in the housing;
   the mouthpiece disposed on an outside of the housing and a mouthpiece cap disposed on the outside of the mouthpiece;
   a head end of said flow passage element connecting to the gas inlet, a tail end of the flow passage element connecting to the mouthpiece via an air channel, and a horizontal portion of the flow passage member having an opening as a drug inlet;
   a drug-dosing metering component disposed below the inverted conical drug powder storage container; and
   said flow passage element connected to the gas inlet, the drug-dosing metering component and the mouthpiece in sequence via the air channel.

2. The dry powder drug-dosing device according to claim 1, wherein said rotational slide passage circuit comprises an upper slide passage and a lower slide passage which are parallel to each other, and a first lifting slide passage and a second lifting slide passage connected to head and tail ends of the upper slide passage and the lower slide passage; said annular manual rotation portion is configured to rotate in a restricted angle and ascend or descend at designated positions on the upper body under the guidance, limitation and effects of the upper slide passage, lower slide passage, the first lifting slide passage, the second lifting slide passage, the sliding block and the first elastic member.

3. The dry powder drug-dosing device according to claim 2, wherein said restricted angle is 120°, said designated positions are the positions of head and tail ends of the upper and lower slide passages.

4. The dry powder drug-dosing device according to claim 2, wherein at least one gas inlet is installed to pass through the housing of said lower slide passage.

5. The dry powder drug-dosing device according to claim 1, wherein at least one gas inlet is installed to pass through the housing of said lower slide passage.

6. The dry powder drug-dosing device according to claim 1, wherein said drug-dosing metering component comprises a ration drug-dosing plate with a central axis, a spring cover under the ration drug-dosing plate and a second elastic member positioned between the lower body and the spring cover;
   a head end of said central axis passes through an upper part of the upper body and a triangle block is provided at a head end of the central axis;
   a triangle hole is provided correspondingly in a center of said annular manual rotation portion;
   a tail end of said central axis is connected to the lower body rotatably;
   three drug-dosing cavities are distributed uniformly along a circumference on the side of the ration drug-dosing plate towards the inverted conical drug powder storage container;
   the drug inlet of said flow passage element is arranged correspondingly to one of the three drug-dosing cavities distributed uniformly along the circumference.

7. The dry powder drug-dosing device according to claim 6, wherein three elastic locating clips are distributed uniformly on the circumference of said ration drug-dosing plate; and three locating grooves are distributed correspondingly in an internal side of the lower body, said elastic locating clips match with the locating grooves to ensure the rotational range of the ration drug-dosing plate is one-third of the circumference every step and a definite signal of rotation in place is given to the user.

8. The dry powder drug-dosing device according to claim 6, wherein said second elastic member is a spring.

9. The dry powder drug-dosing device according to claim 6, wherein the upper part of said upper body is provided with a drying component consisting of a drying tube and granular desiccant therein; said drying tube has an opening in the direction identical to the outlet of the inverted conical drug powder storage container; said drying component and the inverted conical drug powder storage container are arranged in an included angle of 120° relative to the longitudinal central axis of the housing; the opening of said drying component or the outlet of said inverted conical drug powder storage container is arranged to be corresponding to two of three drug-dosing cavities distributed along a circumference of the ration drug-dosing plate of the drug-dosing metering component.

10. The dry powder drug-dosing device according to claim 6, wherein a locking block is set on said annular manual rotation portion, when the mouthpiece cap is in covered status, said locking block cooperates with the mouthpiece cap to form an anti-misrotation mechanical structure, so as to prevent rotation between the annular manual rotation portion and the upper body.

11. A process for inhalation administration using the dry powder drug-dosing device of claim 10, comprising steps of:
   (A1) removing the mouthpiece cap and releasing the anti-misrotation mechanical structure on the annular manual rotation portion;
   (B1) manually rotating the annular manual rotation portion counterclockwise to an extreme position of 120° to enable a first drug-dosing cavity of the ration drug-dosing plate in said drug-dosing metering component to receive a drug supplied from the inverted conical drug powder storage container; the annular manual rotation portion springing upward automatically and the air inlet opening to provide a condition for inhalation administration; meanwhile, the triangle block at the head end of the central axis of said drug-dosing metering component entering the triangle hole in the center of the annular manual rotation portion to provide a precondition for the next rotation of the ration drug-dosing plate;

(C1) manually rotating the annular manual rotation portion reversely to a reverse extreme position of 120°; and the first drug-dosing cavity with drug powder aiming at the drug inlet of the flow passage element to finish the drug supplying process;

(D1) inhaling the drug powder through the mouthpiece, wherein a gas enters the dry powder drug-dosing device from the air inlet and passes the flow passage element to reach the drug inlet, then delivers the drug powder from the first drug-dosing cavity of the ration drug-dosing plate to the patient's mouth via the mouthpiece, and the drug delivering process is finished;

(E1) manually pressing down the annular manual rotation portion to enable a second drug-dosing cavity of the ration drug-dosing plate in said drug-dosing metering component to aim at the drying component for drying and preparing for the next drug-filling; and (F1) covering the mouthpiece cap and restoring the anti-misrotation mechanical structure on the annular manual rotation portion.

12. The dry powder drug-dosing device according to claim 1, wherein said first elastic member is a spring.

13. A process for inhalation administration using the dry powder drug-dosing device of claim 1, comprising steps of:
  (A) removing the mouthpiece cap;
  (B) manually rotating the annular manual rotation portion counterclockwise to an extreme position of 120°; the annular manual rotation portion springing upward automatically;
  (C) manually rotating the annular manual rotation portion reversely to a reverse extreme position of 120°;
  (D) inhaling the drug powder via the mouthpiece;
  (E) pressing down the annular manual rotation portion manually; and
  (F) covering the mouthpiece cap.

14. The dry powder drug-dosing device of claim 1, wherein a vibrating drug-providing unit is equipped on the dry powder drug-dosing device;
  said inverted conical drug powder storage container is disposed in the upper part of the housing;
  an annular manual rotation portion is disposed outside the upper part of the housing;
  a drug-dosing metering component comprising a center rotating axis and a ration drug-dosing plate is disposed under said inverted conical drug powder storage container;
  said center rotating axis of said drug-dosing metering component is connected to said annular manual rotation portion by the meshing of triangle components, the block on the center rotating axis and a hole on the annular manual rotation portion;
  a protruding vibration tooth is disposed at a lower part of said inverted conical drug powder storage container;
  a transmission sleeve is disposed inside a lower end of said annular manual rotation portion;
  an upper end of said transmission sleeve is fixedly connected to the annular manual rotation portion;
  said transmission sleeve is coaxially set outside the central rotating axis;
  a stirring gear is disposed at a lower end of said transmission sleeve; and
  said protruding vibration tooth cooperates with the stirring Gear to form a vibration component to enable an outlet of the inverted conical drug powder storage container to vibrate.

* * * * *